US010703737B2

(12) United States Patent
Menick et al.

(10) Patent No.: US 10,703,737 B2
(45) Date of Patent: Jul. 7, 2020

(54) HDAC INHIBITORS AND USES THEREOF

(71) Applicant: MUSC FOUNDATION FOR RESEARCH DEVELOPMENT, Charleston, SC (US)

(72) Inventors: Donald R. Menick, Isles of Palms, SC (US); Chung-Jen James Chou, Mt. Pleasant, SC (US); Daniel Herr, Johns Island, SC (US); Xiaoyang Li, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days.

(21) Appl. No.: 16/351,809

(22) Filed: Mar. 13, 2019

(65) Prior Publication Data
US 2019/0284154 A1 Sep. 19, 2019

Related U.S. Application Data

(60) Provisional application No. 62/642,150, filed on Mar. 13, 2018.

(51) Int. Cl.
C07D 311/82 (2006.01)
A61P 9/10 (2006.01)

(52) U.S. Cl.
CPC .............. C07D 311/82 (2013.01); A61P 9/10 (2018.01)

(58) Field of Classification Search
CPC .................................. A61P 9/10; C07D 311/82
See application file for complete search history.

(56) References Cited

PUBLICATIONS

Choudhary, C., et al., The growing landscape of lysine acetylation links metabolism and cell signalling. Nat Rev Mol Cell Biol, 2014. 15(8): p. 536-50.
Wellen, K.E., et al., ATP-citrate lyase links cellular metabolism to histone acetylation. Science, 2009. 324(5930): p. 1076-80.
Zhao, S., et al., Regulation of cellular metabolism by protein lysine acetylation. Science, 2010. 327(5968): p. 1000-4.
Choudhary, C., et al., Lysine acetylation targets protein complexes and co-regulates major cellular functions. Science, 2009. 325(5942): p. 834-40.
Koprinarova, M., M. Schnekenburger, and M. Diederich, Role of Histone Acetylation in Cell Cycle Regulation. Curr Top Med Chem. 2016;16(7):732-44.
Swygert, S.G. and C.L. Peterson, Chromatin dynamics: interplay between remodeling enzymes and histone modifications. Biochim Biophys Acta, 2014. 1839(8): p. 728-36.
Corona, D.F., et al., Modulation of ISWI function by site-specific histone acetylation. EMBO Rep, 2002. 3(3): p. 242-7.
Ventura, M., et al., Nuclear translocation of glyceraldehyde-3-phosphate dehydrogenase is regulated by acetylation. Int J Biochem Cell Biol, 2010. 42(10): p. 1672-80.
Ishfaq, M., et al., Acetylation regulates subcellular localization of eukaryotic translation initiation factor 5A (eIF5A). FEBS Lett, 2012. 586(19): p. 3236-41.
Riolo, M.T., et al., Histone deacetylase 6 (HDAC6) deacetylates survivin for its nuclear export in breast cancer. J Biol Chem, 2012. 287(14): p. 10885-93.
Yi, C., et al., Function and molecular mechanism of acetylation in autophagy regulation. Science, 2012. 336(6080): p. 474-7.
Yi, C. and L. Yu, How does acetylation regulate autophagy? Autophagy, 2012. 8(10): p. 1529-30.
Webster, B.R., et al., Regulation of autophagy and mitophagy by nutrient availability and acetylation. Biochim Biophys Acta, 2014. 1841(4): p. 525-34.
Huang, R., et al., Deacetylation of nuclear LC3 drives autophagy initiation under starvation. Mol Cell, 2015. 57(3): p. 456-66.
Allfrey, V.G., R. Faulkner, and A.E. Mirsky, Acetylation and Methylation of Histones and Their Possible Role in the Regulation of RNA Synthesis. Proc Natl Acad Sci U S A, 1964. 51: p. 786-94.
Brownell, J.E., et al., Tetrahymena histone acetyltransferase A: a homolog to yeast Gcn5p linking histone acetylation to gene activation. Cell, 1996. 84(6): p. 843-51.
Gu, W. and R.G. Roeder, Activation of p53 sequence-specific DNA binding by acetylation of the p53 C-terminal domain. Cell, 1997. 90(4): p. 595-606.
Spange, S., et al., Acetylation of non-histone proteins modulates cellular signalling at multiple levels. Int J Biochem Cell Biol, 2009. 41(1): p. 185-98.
Geng, H., et al., HIF1alpha protein stability is increased by acetylation at lysine 709. J Biol Chem, 2012. 287(42): p. 35496-505.
Gronroos, E., et al., Control of Smad7 stability by competition between acetylation and ubiquitination. Mol Cell, 2002. 10(3): p. 483-93.
Samant, S.A., et al., Histone Deacetylase 3 (HDAC3)-dependent Reversible Lysine Acetylation of Cardiac Myosin Heavy Chain Isoforms Modulates Their Enzymatic and Motor Activity. J Biol Chem, 2015. 290(25): p. 15559-69.
Van der Heide, L.P. and M.P. Smidt, Regulation of FoxO activity by CBP/p300-mediated acetylation. Trends Biochem Sci, 2005. 30(2): p. 81-6.
Arbely, E., et al., Acetylation of lysine 120 of p53 endows DNA-binding specificity at effective physiological salt concentration. Proc Natl Acad Sci U S A, 2011. 108(20): p. 8251-6.
Ray, S., et al., Requirement of histone deacetylase1 (HDAC1) in signal transducer and activator of transcription 3 (STAT3) nucleocytoplasmic distribution. Nucleic Acids Res, 2008. 36(13): p. 4510-20.
McKinsey, T.A., Therapeutic potential for HDAC inhibitors in the heart. Annu Rev Pharmacol Toxicol, 2012. 52: p. 303-19.
McKinsey, T.A., Isoform-selective HDAC inhibitors: closing in on translational medicine for the heart. J Mol Cell Cardiol, 2011. 51(4): p. 491-6.
Aune, S.E., et al. Selective inhibition of class I but not class IIb histone deacetylases exerts cardiac protection from Ischemia reperfusion. J Mol Cell Cardiol, 2014. 72: p. 138-45.
Zhao, T.C., et al. Inhibition of histone deacetylases triggers pharmacologic preconditioning effects against myocardial Ischemic injury. Cardiovasc Res, 2007. 76(3): p. 473-81.

(Continued)

Primary Examiner — Valerie Rodriguez-Garcia

(57) ABSTRACT

The present invention relates to histone deacetylase inhibitors, and to pharmaceutical compositions comprising the compounds, useful for the treatment of ischemia-reperfusion injury and for cardioprotection.

4 Claims, 5 Drawing Sheets

(56) References Cited

PUBLICATIONS

Zhang, L., et al., Inhibition of histone deacetylases preserves myocardial performance and prevents cardiac remodeling through stimulation of endogenous angiomyogenesis. J Pharmacol Exp Ther, 2012. 341(1): p. 285-93.

Granger, A., et al., Histone deacetylase inhibition reduces myocardial ischemia-reperfusion injury in mice. FASEB J, 2008. 22(10): p. 3549-60.

Xie, M., et al., Histone deacetylase inhibition blunts ischemia/reperfusion injury by inducing cardiomyocyte autophagy. Circulation, 2014. 129(10): p. 1139-51.

Still, A.J., et al., Quantification of mitochondrial acetylation dynamics highlights prominent sites of metabolic regulation. J Biol Chem, 2013. 288(36): p. 26209-19.

Porter, G.A., et al., SIRT3 deficiency exacerbates ischemia-reperfusion injury: implication for aged hearts. Am J Physiol Heart Circ Physiol, 2014. 306(12): p. H1602-9.

Bochaton, T., et al., Inhibition of myocardial reperfusion injury by ischemic postconditioning requires sirtuin 3-mediated deacetylation of cyclophilin D. J Mol Cell Cardiol, 2015. 84: p. 61-9.

Baines, C.P., et al., Loss of cyclophilin D reveals a critical role for mitochondrial permeability transition in cell death. Nature, 2005. 434(7033): p. 658-62.

Nguyen, T.T., et al., Cyclophilin D modulates mitochondrial acetylome. Circ Res, 2013. 113(12): p. 1308-19.

Anderson, K.A. and M.D. Hirschey, Mitochondrial protein acetylation regulates metabolism. Essays Biochem, 2012. 52: p. 23-35.

Menzies, K.J., et al., Protein acetylation in metabolism—metabolites and cofactors. Nat Rev Endocrinol, 2016. 12(1): p. 43-60.

Ahn, B.H., et al., A role for the mitochondrial deacetylase Sirt3 in regulating energy homeostasis. Proc Natl Acad Sci U S A, 2008. 105(38): p. 14447-52.

Horton, J.L., et al., Mitochondrial protein hyperacetylation in the failing heart. JCI Insight, 2016. 2(1).

Smith, L.E. and M.Y. White, The role of post-translational modifications in acute and chronic cardiovascular disease. Proteomics Clin Appl, 2014. 8(7-8): p. 506-21.

Burwell, L.S., S.M. Nadtochiy, and P.S. Brookes, Cardioprotection by metabolic shut-down and gradual wake-up. J Mol Cell Cardiol, 2009. 46(6): p. 804-10.

Lopaschuk, G.D., et al., Beneficial effects of trimetazidine in ex vivo working ischemic hearts are due to a stimulation of glucose oxidation secondary to inhibition of long-chain 3-ketoacyl coenzyme a thiolase. Circ Res, 2003. 93(3): p. e33-7.

Nielsen, T.T., et al., Metabolic fingerprint of ischaemic cardioprotection: importance of the malate-aspartate shuttle. Cardiovasc Res, 2011. 91(3): p. 382-91.

Chouchani, E.T., et al., Ischaemic accumulation of succinate controls reperfusion injury through mitochondrial ROS. Nature, 2014. 515(7527): p. 431-5.

Burwell LS, Nadtochiy SM and Brookes PS. Cardioprotection by metabolic shut-down and gradual wake-up. J Mol Cell Cardiol. 2009;46:804-10.

Lopaschuk GD, Barr R, Thomas PD and Dyck Jr. Beneficial effects of trimetazidine in ex vivo working ischemic hearts are due to a stimulation of glucose oxidation secondary to inhibition of long-chain 3-ketoacyl coenzyme a thiolase. Circ Res. 2003;93:e33-7.

Nielsen TT, Stottrup NB, Lofgren B and Botker HE. Metabolic fingerprint of ischaemic cardioprotection: importance of the malate-aspartate shuttle. Cardiovasc Res. 2011;91:382-91.

Boylston JA, Sun J, Chen Y, Gucek M, Sack MN and Murphy E. Characterization of the cardiac succinylome and its role in ischemia-reperfusion injury. J Mol Cell Cardiol. 2015;88:73-81.

Rardin MJ, Newman JC, Held JM, Cusack MP, Sorensen DJ, Li B, Schilling B, Mooney SD, Kahn CR, Verdin E and Gibson BW. Label-free quantitative proteomics of the lysine acetylome in mitochondria identifies substrates of SIRT3 in metabolic pathways. Proc Natl Acad Sci U S A. 2013;110:6601-6.

Chouchani et al, Ischaemic accumulation of succinate controls reperfusion injury through mitochondrial ROS. Nature. 2014;515:431-5.

Chen YR and Zweier JL. Cardiac mitochondria and reactive oxygen species generation. Circ Res. 2014;114:524-37.

Garciarena et al, Myocardial reperfusion injury: reactive oxygen species vs. NHE-1 reactivation. Cell Physiol Biochem. 2011;27:13-22.

Kim et al., Substrate and functional diversity of lysine acetylation revealed by a proteomics survey. Mol Cell. 2006;23:607-18.

Choudhary et al., Lysine acetylation targets protein complexes and co-regulates major cellular functions. Science. 2009;325:834-40.

Finley et al., Succinate dehydrogenase is a direct target of sirtuin 3 deacetylase activity. PLoS One. 2011;6:e23295.

Cimen et al., Regulation of succinate dehydrogenase activity by SIRT3 in mammalian mitochondria. Biochemistry. 2010;49:304-11.

Horton et al, Mitochondrial protein hyperacetylation in the failing heart. JCI Insight. 2016;1(2):e84897.

HDAC INHIBITORS AND USES THEREOF

STATEMENT REGARDING FEDERALLY SPONSORED RESEARCH OR DEVELOPMENT

This invention was made with Government support under VA merit award. BX002327-01. Additional support was made by F30 HL129629, T32 GM008716, T32 HL007260, NIH/NCATS Grant Number TL1 TR 000061 and ULI TR 001450. The Government has certain rights in the invention.

FIELD OF THE INVENTION

The invention is directed to histone deacetylase (HDAC) inhibitors and to pharmaceutical compositions comprising the compounds. The compounds and compositions disclosed herein are useful for the treatment of isehemia-reperfusion injury and for cardioprotection.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Recent evidence indicates that histone deacetylase enzymes contribute to ischemia reperfusion (I/R) injury, and pan-HDAC inhibitors have been shown to be cardioprotective when administered either before an ischemic insult or during reperfusion. The inventors have shown previously that selective inhibition of class I HDACs provides superior cardioprotection when compared to pan-HDAC inhibition in a pretreatment model, but selective class I HDAC inhibition has not been tested during reperfusion. Little is known about the exact mechanism by which HDAC inhibition confers cardioprotection against I/R injury.

A need exists in the art, therefore, for HDAC inhibitors for the treatment of I/R injury and cardioprotection.

SUMMARY OF THE INVENTION

The present invention is directed to histone deacetylase inhibitors. The present invention is also directed to a pharmaceutical composition, comprising a therapeutically effective amount of these compounds, or a pharmaceutically acceptable salt thereof, and a pharmaceutically acceptable carrier. The present invention is also directed to the treatment of ischemia-reperfusion injury and to cardioprotection.

DETAILED DESCRIPTION OF THE INVENTION

Figure 1:
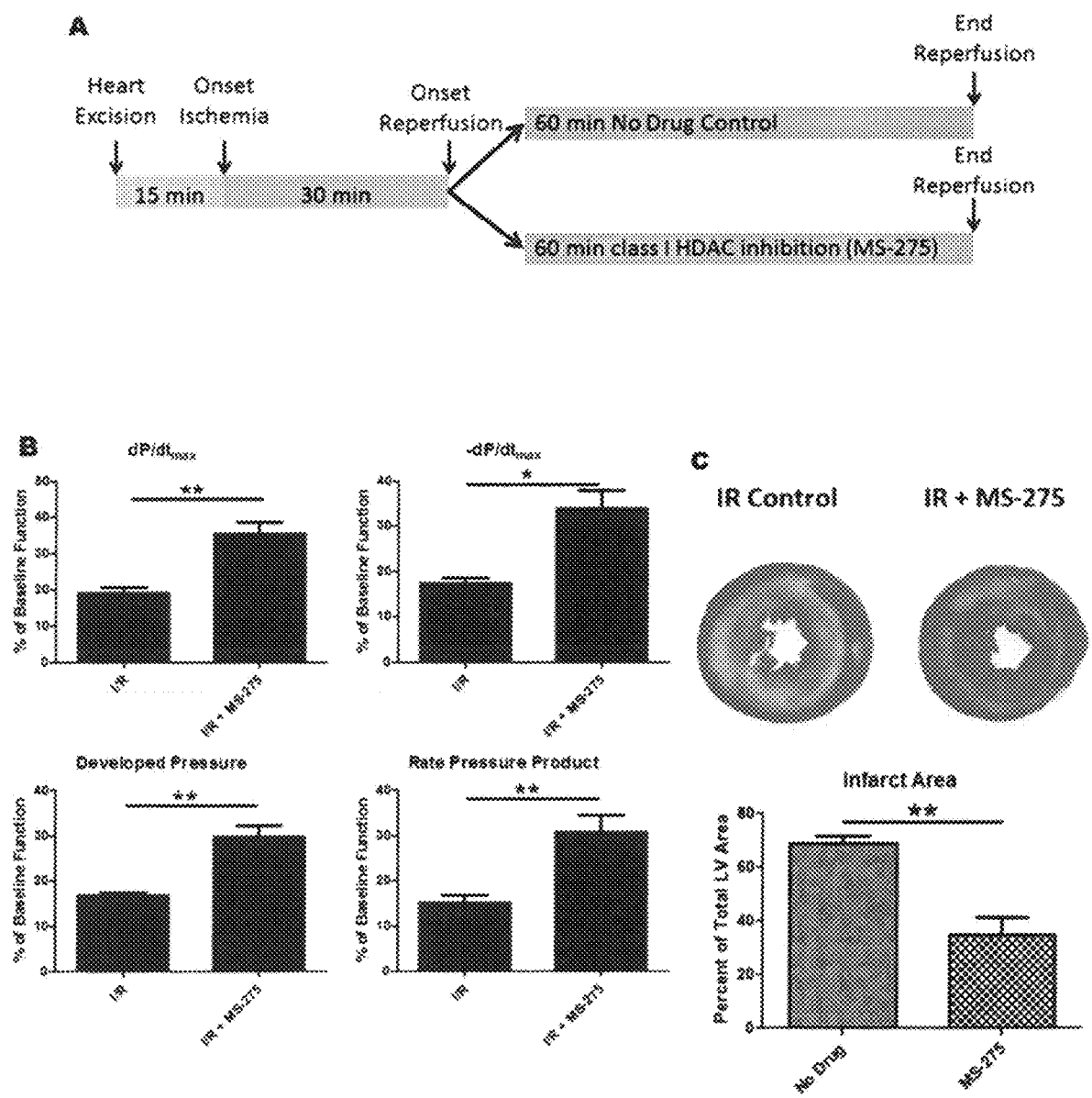
FIG. 1 shows (A) Experimental design for I/R procedures. (B) Graphs represent measurements of left ventricular function after 30 minutes of ischemia and 60 minutes of reperfusion. $dP/dt_{max}$ indicates the rate of pressure development, $dP/dt_{min}$ indicates the rate of pressure relaxation, Developed Pressure was calculated as the difference between the systolic and diastolic pressures, Rate Pressure Product was calculated as the developed pressure multiplied by the heart rate. Measurements were taken at the end of reperfusion. (C) TTC staining for infarct area at the end of reperfusion; yellow/white region indicates area of infarction. Infarct areas were measured using imageJ software. All data are represented as mean+/−S.D. N=4, t-test *p,0.05.

It is to he understood that the descriptions of the present invention have been simplified to illustrate elements that are relevant for a clear understanding of the present invention, while eliminating, for the purpose of clarity, many other elements found in typical pharmaceutical compositions. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The invention is directed to histone deacetylase inhibitors and to pharmaceutical compositions comprising the compounds. The compounds and compositions disclosed herein are useful for the treatment of, for example, ischemia-reperfusion injury.

Lysine acetylation is a reversible post-translational protein modification that occurs on a multitude of proteins and regulates vital cellular processes including metabolism[1.-3], cell cycle regulation[4, 5], chromatin remodeling[6, 7], nuclear transport[4, 8-10], and autophagy[11-14], among others. It was initially proposed[15], and later confirmed that acetylation of histone tails regulates gene expression by loosening chromatin compaction and allowing transcription factors to bind DNA[16]. Eventually, non-histone protein acetylation was also discovered, starting with p53[17] and expanding to non-histone proteins throughout the cell[18]. As the field has expanded, it has come to be appreciated that the acetylation state of non-histone proteins and enzymes can dramatically affect characteristics of the acetylated proteins, including protein stability[19, 20], enzymatic activity[21, 22], DNA binding[23], and intracellular localization.[24]. These changes in protein characteristics can have a profound effect on cellular processes, including those determining the fate of cells subjected to injury.

Lysine acetylation occurs via the addition of an acetyl group from acetyl-CoA to the ε-amino moiety of lysine residues in a reaction catalyzed by histone acetyltransferases (HATs). The removal of acetyl groups, termed deacetylation, is achieved by histone deacetylases (HDACs). HDACs consist of 4 classes, delineated based on their similarity to histone deacetylase enzymes in yeast. HDACs 1, 2, 3, and 8 comprise the class I HDACs. Class II HDACs are sub-grouped into class IIa (HDACs 4, 5, 7, and 9), and class IIb HDACs (HDACs 6 and 10). Class III HDACs are the sirtuin family, differentiated from the other classes because they use $NAD^+$ as a cofactor. HDAC11 is the sole known class IV HDAC. In the last two decades, the function of HDACs and their promise as a treatment target in cardiovascular disease has become a topic of great interest in cardiac research[25, 26]. Accordingly, the pharmacological inhibition of HDAC activity has been shown to be beneficial in animal models of multiple cardiac pathologies, though these discoveries have yet to be translated to the clinic.

HDAC inhibition preceding ischemia reperfusion (I/R) injury in the heart can preserve left ventricular function and myocardial survival[27-29]. Importantly, the inventors demonstrated that the selective inhibition of class I HDACs was more effective than pan-HDAC inhibition in preserving myocardial viability and function in the setting of I/R injury. Recently, pan-HDAC inhibition solely during the reperfusion phase of I/R injury was shown to preserve myocardial function in multiple animal models, although the exact mechanisms behind this cardioprotection have yet to be fully elucidated[30, 31].

The inventors utilized a Langendorff isolated heart model to test the hypothesis that selective pharmacological class I HDAC inhibition during the reperfusion phase alone would confer cardioprotection from PR injury. In doing so, the inventors discovered that HDAC1 localizes to the mitochondria of cardiac myocytes and modifies oxidative metabolism.

Abbreviations and Definitions:

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, $10^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

HAT refers to histone acetyltransferase enzyme.
HDAC refers to histone deacetylase enzyme.
I/R refers to ischemia reperfusion injury.
dP/dt refers to rate of LV pressure generation.
$dP/dt_{min}$ refers to rate of LV pressure relaxation.
TTC refers to 2,3,5-triphenyltetrazolium chloride.
mPTP refers to mitochondrial permeability transition pore.
sI/R refers to simulated ischemia reperfusion injury in vitro.
OCR refers to oxygen consumption rate.
MS-275 is the compound having the following structure:

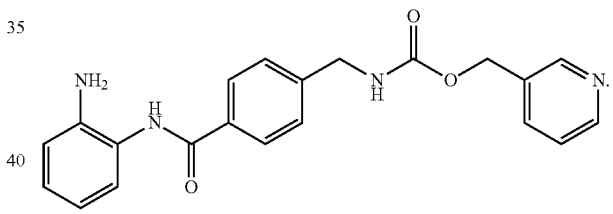

A compound according to the invention is inherently intended to comprise all stereochemically isomeric forms thereof. The term "stereochemically isomeric forms" as used hereinbefore or hereinafter defines all the possible stereoisomeric forms which the compounds of formula (I) and their N-oxides, pharmaceutically acceptable salts or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cis- or trans-configuration. Compounds encompassing double bonds can have an E (entgegen) or Z (zusanunen)-stereochemistry at said double bond. The terms cis, trans, R, S, E and Z are well known to a person skilled in the art.

Stereochemically isomeric forms of the compounds of formula (I) are obviously intended to be embraced within the scope of this invention. Of special interest are those compounds of formula (I) which are stereochemically pure.

Following CAS-nomenclature conventions, when two stereogenic centers of known absolute configuration are present in a molecule, an R or S descriptor is assigned (based on. Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, When a compound of formula (I) is for instance specified as (R,S), this means that the compound is substantially free of the (S,R) isomer.

The compounds of formula (I) may be synthesized in the form of mixtures, in particular racemic mixtures, of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (I) are meant to comprise those compounds of formula (I) wherein e.g. an enol group is converted into a keto group (keto-enol tautomerism). Tautomeric forms of the compounds of formula (I) or of intermediates of the present invention are intended to be embraced by the ambit of this invention.

A "patient" is a mammal, e.g., a human, mouse, rat, guinea pig, dog, cat, horse, cow, pig, or non-human primate, such as a monkey, chimpanzee, baboon or rhesus monkey, and the terms "patient" and "subject" are used interchangeably herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body, Dosage and Administration:

The compounds of the present invention may be formulated in a wide variety of oral administration dosage forms and carriers. Oral administration can be in the form of tablets, coated tablets, drages, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable through veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingedient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or fumed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3(4-hydroxybenzoyl)berizoic acid, cinnamic acid, mandelic acid, methanesulfonic acid, ethanesulfonic acid, 1,2-ethane-disulfonic acid, 2-hydroxyethanestilfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, arid other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be-presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease or disorder in an individual. The dose will be adjusted to the individual requirements in each particular case. That dosage can vary within wide limits depending upon numerous factors such as the severity of the disease to be treated, the age and general health condition of the patient, other medicaments with Which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight, and most preferred 1.0 and about 15 mg/kg body weight per day. Thus, for administration to a 70 kg person, the dosage range in one embodiment would be about 70 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Compounds of the present invention can be prepared beginning with commercially available starting materials and utilizing general synthetic techniques and procedures known to those skilled in the art. Chemicals may be purchased from companies such as for example SigmaAldrich, Argonaut Technologies, NWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; and Waters Corporation, Milford, Mass. Biotage, ISCO and Analogix columns are pre-packed silica gel columns used in standard chromatography.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

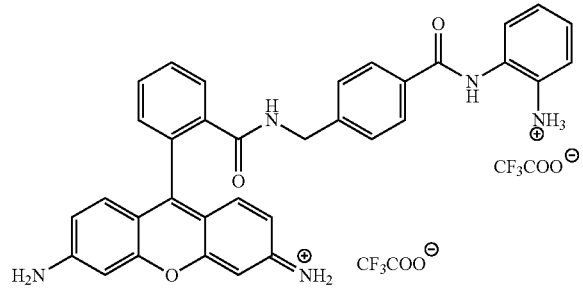

2-(4-((2-(6-amino-3-iminio-3H-xanthen-9-yl)benzamido)methyl)benzamido) benzenaminium 2,2,2-trifluoroacetate (LL66)

4-(aminomethyl)benzoic acid (755 mg, 5 mmol) was dissolved in 15 mL 1 mol/L NaOH aqueous solution, to which was added 1308 mg Boc$_2$O and 2 mL THF. The mixture was stirred overnight and THF condensed under vacuum. The residue was acidification by diluted hydrochloric acid and the resulting white solid was filtered to yield Boc-protected intermediate. The Boc-protected compound, 1925 mg TBTU and 1 mL TEA were dissolved in 50 mL DCM. 30 mins later, 1,2-diaminobenzene (650 mg, 6 mM) was added and the mixture was allowed to stir at room temperature overnight. Volatiles were removed under vacuum, the residue was recrystallized by ethyl estate and hexane to yield a white solid. This was dissolved in 10 mL mixed solution of DCM and TFA (1:1), the solution was stirred at room temperature for 1 hour. The volatiles were evaporated under vacuum to afford a color less oil. 110 mg oil was dissolved in 5 mL DMF then 193 mg N,N-Diisopropylethylamine and 114 mg Rhodamine 110 chloride was added. After the reaction finished, 30 mL water was added and the mixed solution was extracted by ethyl estate. The organic phase was dried by MgSO$_4$ and evaporated under vacuum. The crude residue was purified on C18 reverse phase columns eluted with acetonitrile and water (containing 0.2% TFA) to yield the pure product.

| Cpd No. | IC$_{50}$ (μM) | | |
|---|---|---|---|
|  | HDAC1 | HDAC2 | HDAC3 |
| LL66 | 4.02 | 3.48 | 0.355 |

The NMR and mass spectrometry characterization of LL-66 is as follows:
$^1$H NMR (400 MHz, DMSO-d$^6$) δ 9.57 (s, 1H), 7.83 (d, J=6.6 Hz, 1H), 7.67 (d, 8.2 Hz, 2H), 7.60-7.50 (m, 2H), 7.12 (d, J=7.3 Hz, 1H), 7.03-6.91 (m, 5H), 6.77 (dd, J=8.0, 1,1 Hz, 1H), 6.60 (t, J=7.5 Hz, 1H), 6.31 (d, J=1.8 Hz, 2H), 6.16-6.11 (m, 4H), 4.15 (s, 2H). ESI/MS m/z: 554.17 [H+H]$^+$

Example 2

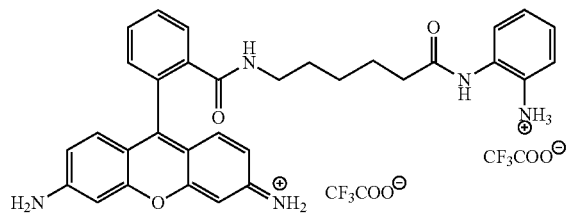

2-(6-(2-(6-amino-3-iminio-3H-xanthen-9-yl)benzamido)hexanamido) benzenaminium 2,2,2-trifluoroacetate (LL38)

6-aminohexanoic acid (655 mg, 5 mmol) was dissolved in 15 mL 1 mol/L NaOH aqueous solution, to which was added 1308 mg Boc$_2$O and 2 mL THF. The mixture was stirred overnight and THF condensed under vacuum. The residue was acidification by diluted hydrochloric acid and the resulting white solid was filtered to yield Boc-protected intermediate. The Boc-protected compound, 1925 rag TBTU and 1 mL TEA were dissolved in 50 mL DCM. 30 mins later, 1,2-diaminobenzene (650 mg, 6 mM) was added and the mixture was allowed to stir at room temperature overnight. Volatiles were removed under vacuum, the residue was recrystallized by ethyl estate and hexane to yield a white solid. This was dissolved in 10 mL mixed solution of DCM and TFA (1:1), the solution was stirred at room temperature for 1 hour. The volatiles were evaporated under vacuum to afford a color less oil. 100 mg oil was dissolved in 5 mL DMF then 193 mg N,N-Diisopropylethylamine and 114 mg Rhodamine 110 chloride was added. After the reaction finished, 30 mL water was added and the mixed solution was extracted by ethyl estate. The organic phase was dried by MgSO$_4$ and evaporated under vacuum. The crude residue was purified on C18 reverse phase columns eluted with acetonitrile and water (containing 0.2% TFA) to yield the pure product.

| Cpd No. | IC$_{50}$ (μM) | | |
|---|---|---|---|
|  | HDAC1 | HDAC2 | HDAC3 |
| LL38 | 1.26 | 0.49 | 0.18 |

Example 3

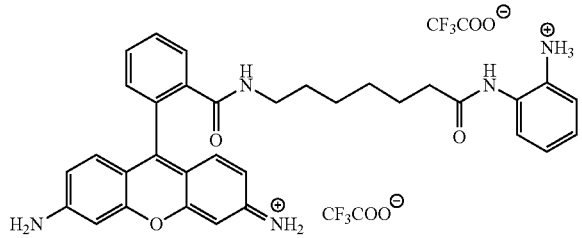

2-(7-(2-(6-amino-3iminio-3H-xanthen-9-yl)benzamido)heptanamido) benzenaminium 2,2,2-trifluoroacetate (LL45)

7-aminoheptanoic acid (725 mg, 5 mmol) was dissolved in 15 mL 1 mol/L NaOH aqueous solution, to which was added 1308 mg Boc$_2$O and 2 mL THF. The mixture was stirred overnight and THF condensed under vacuum. The residue was acidification by diluted hydrochloric acid and the resulting white solid was filtered to yield Boc-protected intermediate. The Boc-protected compound, 1925 mg TBTU and 1 mL TEA were dissolved in 50 mL DCM. 30 mins later, 1,2-diaminobenzene (650 mg, 6 mM) was added and the mixture was allowed to stir at room temperature overnight. Volatiles were removed under vacuum, the residue was recrystallized by ethyl estate and hexane to yield a white solid. This was dissolved in 10 mL mixed solution of DCM and TFA (1:1), the solution was stirred at room temperature for 1 hour. The volatiles were evaporated under vacuum to afford a color less oil. 110 mg oil was dissolved in 5 mL DMF then 193 mg N,N-Diisopropylethylamine and 114 mg Rh.odamine 110 chloride was added. After the reaction finished, 30 mL water was added and the mixed solution was extracted by ethyl estate. The organic phase was dried by MgSO$_4$ and evaporated under vacuum. The crude residue was purified on C18 reverse phase columns eluted with acetonitrile and water (containing 0.2% TFA) to yield the pure product.

| Cpd No. | IC$_{50}$ (μM) | | |
|---|---|---|---|
| | HDAC1 | HDAC2 | HDAC3 |
| LL45 | 1.95 | 2.46 | 0.055 |

Example 4

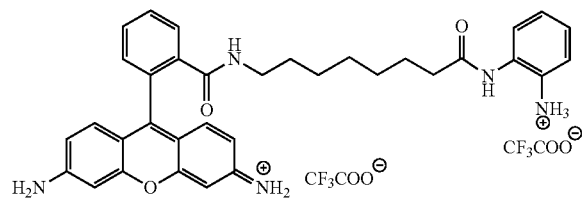

2-(8-(2-(6-amino-3-iminio-3H-xanthen-9-yl)benzamido)octanamido) benzenaminium 2,2,2-trifluoroacetate (LL130)

8-aminooctanoic acid (795 mg, 5 mmol) was dissolved in 15 mL 1 mol/L NaOH aqueous solution, to which was added 1308 mg Boc$_2$O and 2 mL THF. The mixture was stirred overnight and THF condensed under vacuum. The residue was acidification by diluted hydrochloric acid and the resulting white solid was filtered to yield Boc-protected intermediate. The Boc-protected. compound, 1925 mg TBTU and 1 mL TEA were dissolved in 50 mL DCM. 30 mins later, 1,2-diaminobenzene (650 mg, 6 mM) was added and the mixture was allowed to stir at room temperature overnight. Volatiles were removed under vacuum, the residue was recrystallized by ethyl estate and hexane to yield a white solid. This was dissolved in 10 mL mixed solution of DCM and TFA (1:1), the solution was stirred at room temperature for 1 hour. The volatiles were evaporated under vacuum to afford a color less oil. 110 mg oil was dissolved in 5 mL DMF then 193 mg N,N-Diisopropylethylamine and 114 mg Rhodamine 110 chloride was added. After the reaction finished, 30 mL water was added and the mixed solution was extracted by ethyl estate. The organic phase was dried by MgSO$_4$ and evaporated under vacuum. The crude residue was purified on C18 reverse phase columns eluted with acetonitrile and water (containing 0.2% TFA) to yield the pure product.

Example 5

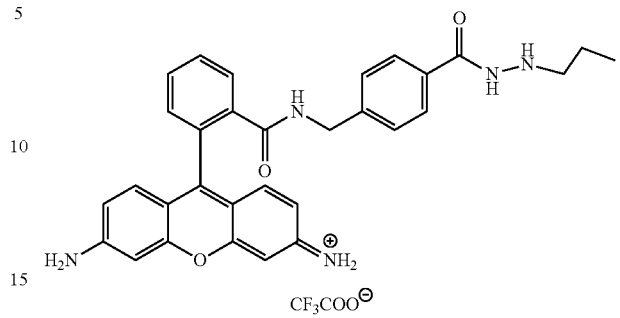

6-amino-9-(2-((4-(2-propylhydrazine-1-carbonyl)benzyl)carbamoyl)phenyl)-3H-xanthen-3-iminium 2,2,2-trifluoroacetate (LL65)

4-(aminomethyl)benzoic acid (755 mg, 5 mmol) was dissolved in 15 mL 1 mol/L NaOH aqueous solution, to which was added 1308 mg Boc$_2$O and 2 mL THF. The mixture was stirred overnight and THF condensed under vacuum. The residue was acidification by diluted hydrochloric acid and the resulting white solid was filtered to yield Boc-protected intermediate. The Boc-protected compound, 1925 mg TBTU and 1 mL TEA were dissolved in 50 mL DCM. 30 mins later, Hydrazinehydrate (0.5 g, 10 mM) was added and the mixture was allowed to stir at room temperature overnight. Volatiles were removed under vacuum, the residue was recrystallized by ethyl estate and hexane to yield a white solid. This compound and 348 mg propionaldehyde were dissolved in 50 mL ethanol and reacted for 2 hours. Vacuum evaporation afforded the desired intermediate which was dissolved in 50 mL methanol, to this solution was added 5 mg methyl orange and 1256 mg sodium cyanoborohydride. Mixture of methanol and concentrated hydrochloric acid (1:1) was added dropwise until the solution turned and stayed red. 6 hours later, volatiles were removed under vacuum and purified on reverse phase columns eluted with acetonitrile and water to yield pure product. This intermediate was dissolved in 10 mL mixed solution of DCM and TFA (1:1), the solution was stirred at room temperature for 1 hour. The volatiles were evaporated under vacuum to afford a color less oil. 105 mg oil was dissolved in 5 mL DMF then 193 mg N,N-Diisopropylethylamine and 114 mg Rhodamine 110 chloride was added. After the reaction finished, 30 mL water was added and the mixed solution was extracted by ethyl estate. The organic phase was dried by MgSO$_4$ and evaporated under vacuum. The crude residue was purified on C18 reverse phase columns eluted with acetonitrile and water (containing 0.2% TFA) to yield the pure product.

| Cpd No. | IC$_{50}$ (μM) | | |
|---|---|---|---|
| | HDAC1 | HDAC2 | HDAC3 |
| LL130 | 4.73 | 5.17 | 0.152 |

| Cpd No. | IC$_{50}$ (μM) | | |
|---|---|---|---|
| | HDAC1 | HDAC2 | HDAC3 |
| LL65 | 0.276 | 0.849 | 0.036 |

Example 6

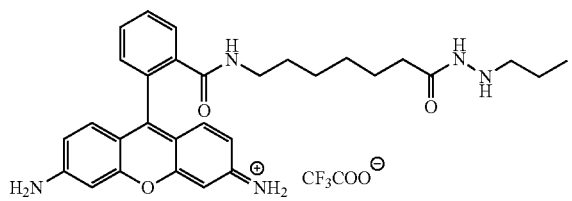

6-amino-9-(2-((7-oxo-7-(2-propylhydrazinyl)heptyl)carbamoyl)phenyl)-3H-xanthen-3-iminium 2,2,2-trifluoroacetate (LL142)

7-aminoheptanoic acid (725 mg, 5 mmol) was dissolved in 15 mL 1 mol/L NaOH aqueous solution, to which was added 1308 mg $Boc_2O$ and 2 mL THF. The mixture was stirred overnight and THF condensed under vacuum. The residue was acidification by diluted hydrochloric acid and the resulting white solid was filtered to yield Boc-protected intermediate. The Boc-protected compound, 1925 mg TBTU and 1 mL TEA were dissolved in 50 mL DCM. 30 mins later, Hydrazinehydrate (500 mg, 10 mM) was added and the mixture was allowed to stir at room temperature overnight. Volatiles were removed under vacuum, the residue was recrystallized by ethyl estate and hexane to yield a white solid. This compound and 348 mg propionaldehyde were dissolved in 50 mL ethanol and reacted for 2 hours. Vacuum evaporation afforded the desired intermediate which was dissolved in 50 mL methanol, to this solution was added 5 mg methyl orange and 1256 mg sodium cyanoborohydride. Mixture of methanol and concentrated hydrochloric acid (1:1) was added dropwise until the solution turned and stayed red. 6 hours later, volatiles were removed under vacuum and purified on reverse phase columns eluted with acetonitrile and water to yield pure product. This intermediate was dissolved in 10 mL mixed solution of DCM and TFA (1:1), the solution was stirred at room temperature for 1 hour. The volatiles were evaporated under vacuum to afford a color less oil. 100 mg oil was dissolved in 5 mL DMF then 193 mg N,N-Diisopropylethylamine and 114 mg Rhodamine 110 chloride was added. After the reaction finished, 30 mL water was added and the mixed solution was extracted by ethyl estate. The organic phase was dried by $MgSO_4$ and evaporated under vacuum. The crude residue was purified on C18 reverse phase columns eluted with acetonitrile and water (containing 0.2% TFA) to yield the pure product.

| Cpd No. | IC$_{50}$ (µM) | | |
|---|---|---|---|
| | HDAC1 | HDAC2 | HDAC3 |
| LL142 | 0.111 | 0.460 | 0.006 |

Example 7

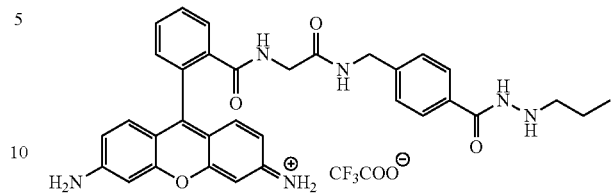

6-amino-9-(2-((2-oxo-2-((4-(2-propylhydrazine-1-carbonyl)benzyl)amino)ethyl)carbamoyl)phenyl)-3H-xanthen-3-iminium 2,2,2-trifluoroacetate (LL115)

Glycine (375 mg, 5 mmol) was dissolved in 15 mL 1 mol/L NaOH aqueous solution, to which was added 1308 mg $Boc_2O$ and 2 mL THF. The mixture was stirred overnight and THF condensed under vacuum. The residue was acidification by diluted hydrochloric acid and the resulting white solid was filtered to yield Boc-protected glycine. 4-(aminomethyl)benzoic acid (1057 mg, 7 mmol) was suspended in 50 mL methanol, to which was added 1.2 g acetyl chloride. The mixture was refluxed for 5 hours and the volatiles condensed under vacuum to yield (4-(methoxycarbonyl)phenyl)methanaminium chloride. The Boc-protected glycine, 1925 mg TBTU and 1 mL TEA were dissolved in 50 mL DCM. 30 mins later, (4-(methoxycarbonyl)phenyl)methanaminium chloride (1206 mg, 6 mM) was added and the mixture was allowed to stir at room temperature overnight. Volatiles were removed under vacuum, the residue was recrystallized by ethyl estate and hexane to yield a white solid. This intermediate was refluxed with Hydrazinehydrate (500 mg, 10 mM) in methanol for 48 h. After removing volatiles, residue was dissolved in 50 mL ethanol with 348 mg propionaldehyde. 2 hours later, vacuum evaporation afforded the desired intermediate which was dissolved in 50 mL methanol, to this solution was added 5 mg methyl orange and 1256 mg sodium cyanoborohydride. Mixture of methanol and concentrated hydrochloric acid (1:1) was added dropwise until the solution turned and stayed red. After 6 hours, methanol were removed under vacuum and purified on reverse phase columns eluted with acetonitrile and water to yield pure product. This intermediate was dissolved in 10 mL mixed solution of DCM and TFA (1:1), the solution was stirred at room temperature for 1 hour. The volatiles were evaporated under vacuum to afford a color less oil. 100 mg oil was dissolved in 5 mL DMF then 193 mg N,N-Diisopropylethylamine and 114 mg Rhodamine 110 chloride was added. After the reaction finished, 30 mL water was added and the mixed solution was extracted by ethyl estate. The organic phase was dried by $MgSO_4$ and evaporated under vacuum. The crude residue was purified on C18 reverse phase columns eluted with acetonitrile and water (containing 0.2% TFA) to yield the end product.

| Cpd NO. | IC$_{50}$ (µM) | | |
|---|---|---|---|
| | HDAC1 | HDAC2 | HDAC3 |
| LL115 | 0.041 | 0.209 | 0.005 |

Example 8

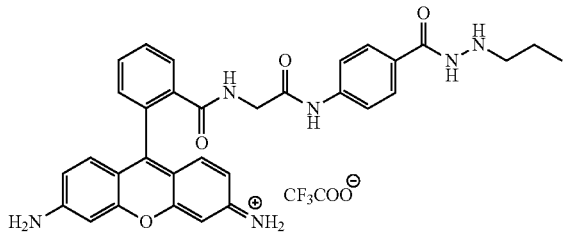

6-amino-9-(2-((2-oxo-2-((4-(2-propylhydrazine-1-carbonyl)phenyl)amino)ethyl) carbamoyl)phenyl)-3H-xanthen-3-iminium 2,2,2-trifluoroacetate (LL162)

Glycine (375 mg, 5 mmol) was dissolved in 15 mL 1 mol/L NaOH aqueous solution, to which was added 1308 mg $Boc_2O$ and 2 mL THF. The mixture was stirred overnight and THF condensed under vacuum. The residue was acidification by diluted hydrochloric acid and the resulting white solid was filtered to yield Boc-protected glycine. 4-aminobenzoic acid (959 mg, 7 mmol) was suspended in 50 mL methanol, to which was added 1.2 g acetyl chloride. The mixture was refluxed for 5 hours and the volatiles condensed under vacuum to yield 4-(methoxycarbonyl)benzenaminium chloride. The Boc-protected glycine, 1925 mg TBTU and 1 mL TEA were dissolved in 50 mL DCM. 30 mins later, 4-(methoxycarbonyl)benzenaminium chloride (1122. mg, 6 mM) was added and the mixture was allowed to stir at room temperature overnight. Volatiles were removed under vacuum, the residue was recrystallized by ethyl estate and hexane to yield a white solid. This intermediate was refluxed with Hydrazinehydrate (500 mg, 10 mM) in methanol for 48 h. After removing volatiles, residue was dissolved in 50 mL ethanol with 348 mg propionaldehyde. 2 hours later, vacuum evaporation afforded the desired intermediate which was dissolved in 50 mL methanol, to this solution was added 5 mg methyl orange and 1256 mg sodium cyanoborohydride. Mixture of methanol and concentrated hydrochloric acid (1:1) was added dropwise until the solution turned and stayed red. After 6 hours, methanol were removed under vacuum and purified on reverse phase columns eluted with acetonitrile and water to yield pure product. This intermediate was dissolved in 10 mL mixed solution of DCM and TFA (1:1), the solution was stirred at room temperature for 1 hour. The volatiles were evaporated under vacuum to afford a color less oil. 100 mg oil was dissolved in 5 mL DMF then 193 mg N,N-Diisopropylethylamine and 114 mg Rhodamine 110 chloride was added. After the reaction finished, 30 mL water was added and the mixed solution was extracted by ethyl estate. The organic phase was dried by $MgSO_4$ and evaporated under vacuum. The crude residue was purified on C18 reverse phase columns eluted with acetonitrile and water (containing 0.2% TFA) to yield the end product.

| Cpd No. | $IC_{50}$ (μM) | | |
|---|---|---|---|
| | HDAC1 | HDAC2 | HDAC3 |
| LL162 | 0.124 | 0.468 | 0.007 |

Example 9

Biological Models

Inhibition of Class I HDAC Activity at Reperfusion Preserves Left Ventricular Function and Viable Myocardium Post I/R-Injury Ex Vivo.

HDAC activity increases in response to I/R injury[30]. The inventors and others have shown that I/R injury can be limited by administrating pharmacological HDAC inhibitors to animals before subjecting them to I/R injury either ex vivo or in vivo[27-29]. Importantly, the inventors' work was the first to use class selective pharmacological HDAC inhibition to definitively show that class I HDACs are primarily responsible for the detrimental effects of HDAC activity during early reperfusion injury. While some studies have recently examined the effect of pan-HDAC inhibition as a postconditioning stimulus (i.e. administration only during the reperfusion phase of I/R injury), none have selectively examined the effect of class I HDAC inhibition[30, 31].

To test whether selective class I HDAC inhibition can postcondition the heart against lift injury, the inventors isolated hearts from Sprague-Dawley rats and perfused them using a constant pressure Langendorff apparatus. After 15 minutes of equilibration, the inventors subjected the hearts to 30 minutes of ischemia, followed by 60 minutes of reperfusion. The selective class I HDAC inhibitor MS-275 was administered throughout the reperfusion phase and compared to drug-free control hearts (FIG. 1A). In order to measure left ventricular functional performance, a saline-filled balloon was inserted into the left ventricle and attached to a pressure transducer. The inventors observed a significant preservation of multiple parameters of ventricular function with class I HDAC inhibition during reperfusion alone; including the rate of pressure generation ($dP/dt_{max}$), rate of pressure relaxation ($-dP/dt_{max}$), developed pressure and rate pressure product (FIG. 1B). At the conclusion of the 60 minute reperfusion period, hearts were removed from the perfusion column and sliced into 2 mm transverse sections using a tissue slicing matrix. Hearts were then incubated in 2,3,5-triphenyltetrazolium chloride (ITC) in order to determine the amount of infarcted myocardium. MS-275 significantly reduced infarct area when compared to control hearts (FIG. 1C).

HDAC1 Localizes to the Mitochondria in Normal Rat Ventricular Cardiac Tissue.

Given the very short timeframe (60 minutes) within which selective class I HDAC inhibition attenuated reperfusion injury, the inventors decided to focus on extra-nuclear survival mechanisms that may be affected by protein acetylation. Many of the critical pathways determining the acute myocardial response to I/R injury either originate within the mitochondria or externally target the mitochondrial permeability transition pore (mPTP). It has recently been discovered that acetylation is a very important regulator of enzymatic function and protein-protein interaction in the mitochondria [1, 4, 32]. Other studies have demonstrated a potential role for mitochondrial protein acetylation in the response to I/R injury, with most studies focusing on the effects of SIRT3-mediated acetylation in I/R [33, 34]. Interestingly, recent work utilizing a Cyclophilin D knockout, a model that is resistant to ischemia-reperfusion injury [35], demonstrated increased acetylation of mitochondrial proteins [36]. Importantly, only a small percentage of the identified peptides were SIRT3 substrates, leaving open the possibility of another mitochondrial deacetylase.

Figure 2:
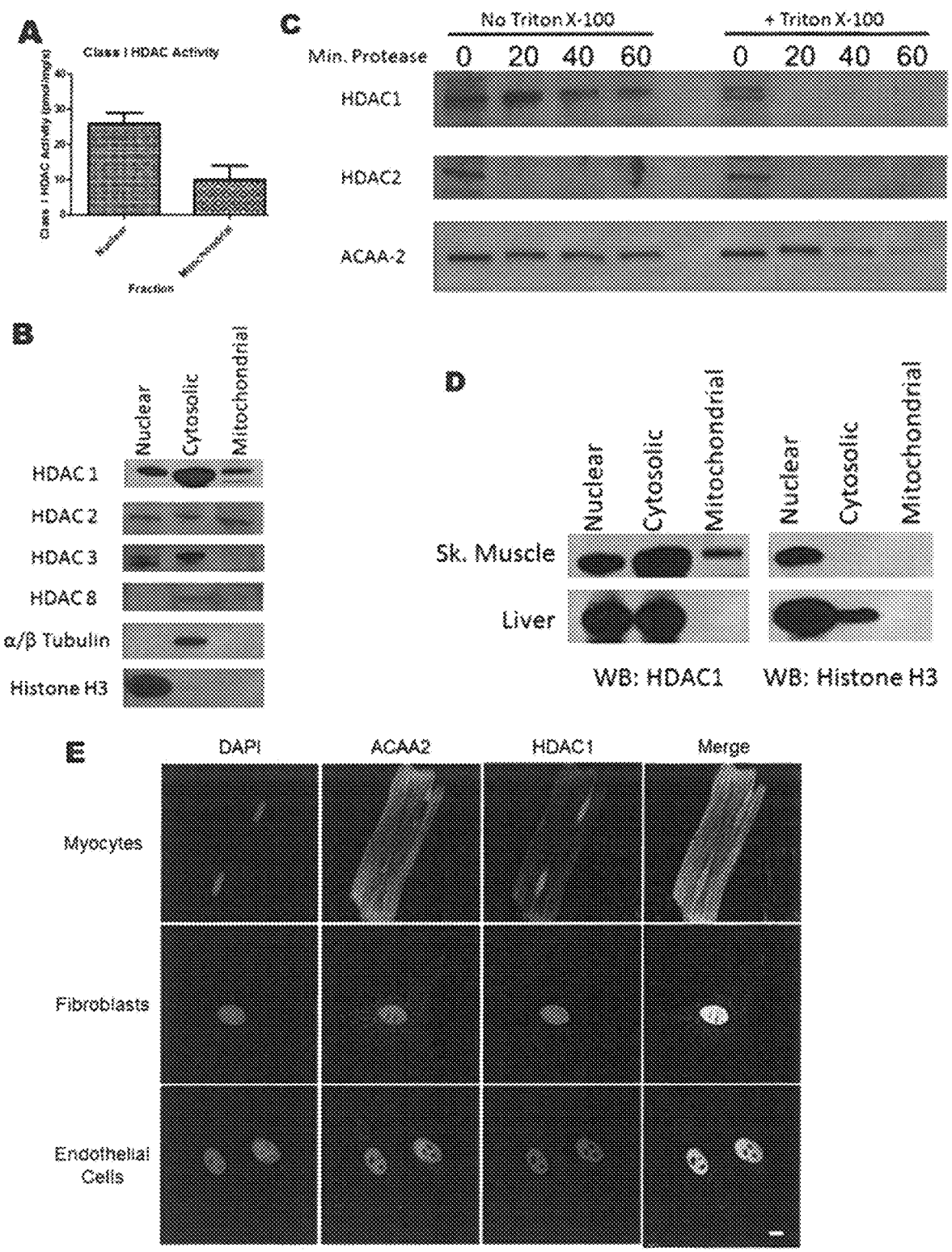
FIG. 2 shows (A) Class I HDAC activity in whole heart nuclear and mitochondrial isolates. (B) Western blotting for class I HDACs in whole heart nuclear, cytoplasmic, and mitochondrial isolates. (C) Proteinase K digestion of whole heart mitochondrial isolates. (D) Western blotting for HDAC 1 in skeletal muscle and liver mitochondrial isolates. (E) Staining for HDAC1 and ACAA2 in cardiac myocytes, fibroblasts and endothelial cells. N=3 per group for all experiments.

Given the role of mitochondria in early cell death signaling, and the role of acetylation in regulating metabolic pathways, the inventors decided to investigate the possibility that class I HDACs either directly or indirectly modify the acetylation of mitochondrial proteins, thus altering the mitochondrial response to I/R injury. To do this, mitochondria were isolated from mouse hearts and subjected to a class I HDAC activity assay. Surprisingly, robust class I HDAC activity was detected in the mitochondrial samples (FIG. 2A). To determine which class I HDACs were present in the mitochondrial isolates, western blotting was performed for each class I HDAC. HDAC1 and HDAC2 were both detected in the mitochondrial isolates. While HDAC3 and HDAC8 were not (FIG. 2B). To further interrogate the localization of HDAC1. and HDAC2, mitochondrial isolates were subjected to proteinase K digestion. HDAC1 was still detected after 60 minutes of proteinase K digestion, supporting its localization within the mitochondria, while HDAC2 was rapidly digested, suggesting that it associates with the outer mitochondrial membrane, ACAA2, the final enzyme in the fatty acid β-oxidation pathway, was used as a marker for the mitochondrial matrix. Addition of triton-X100 to disrupt mitochondrial membranes demonstrated that HDAC1 is susceptible to proteinase K digestion. (FIG. 2C).

This is the first demonstration of a class I HDAC; in mammalian mitochondria. Therefore, inventors decided to test other rat tissues to determine if mitochondrial localization of HDAC1 is widespread, restricted to muscle, or restricted to the heart. Mitochondria were isolated from rat quadriceps and liver and subjected to western blotting for HDAC1. Intriguingly, HDAC1 was detected in the mitochondrial isolate from skeletal muscle, while it was absent from the mitochondria of the liver (FIG. 2D).

HDAC1 Localizes to the Mitochondria of Cardiac Myocytes, but not Fibroblasts or Endothelial Cells In order to further characterize the distribution of HDAC1 within the heart, the inventors subjected cardiac myocytes, fibroblasts, and endothelial cells to immunofluorescence staining for HDAC1 and the mitochondrial marker ACAA2. In the myocytes, HDAC1 was robustly detected within the nucleus, as expected. Confirming the results of the inventors' biochemical studies, HDAC1 was also detected throughout the myocyte in a pattern that closely overlaps with the mitochondrial marker ACAA2 (FIG. 2E). Fibroblasts and endothelial cells show canonical HDAC1 localization only in the nucleus, with no HDAC1 detected in the cytoplasm or mitochondria (FIG. 2E).

Mitochondria-Targeted Class I HDAC Inhibition Results in Significant P)reservation of LV Function and Myocyte Viability Post-I/R Injury.

Figure 3:
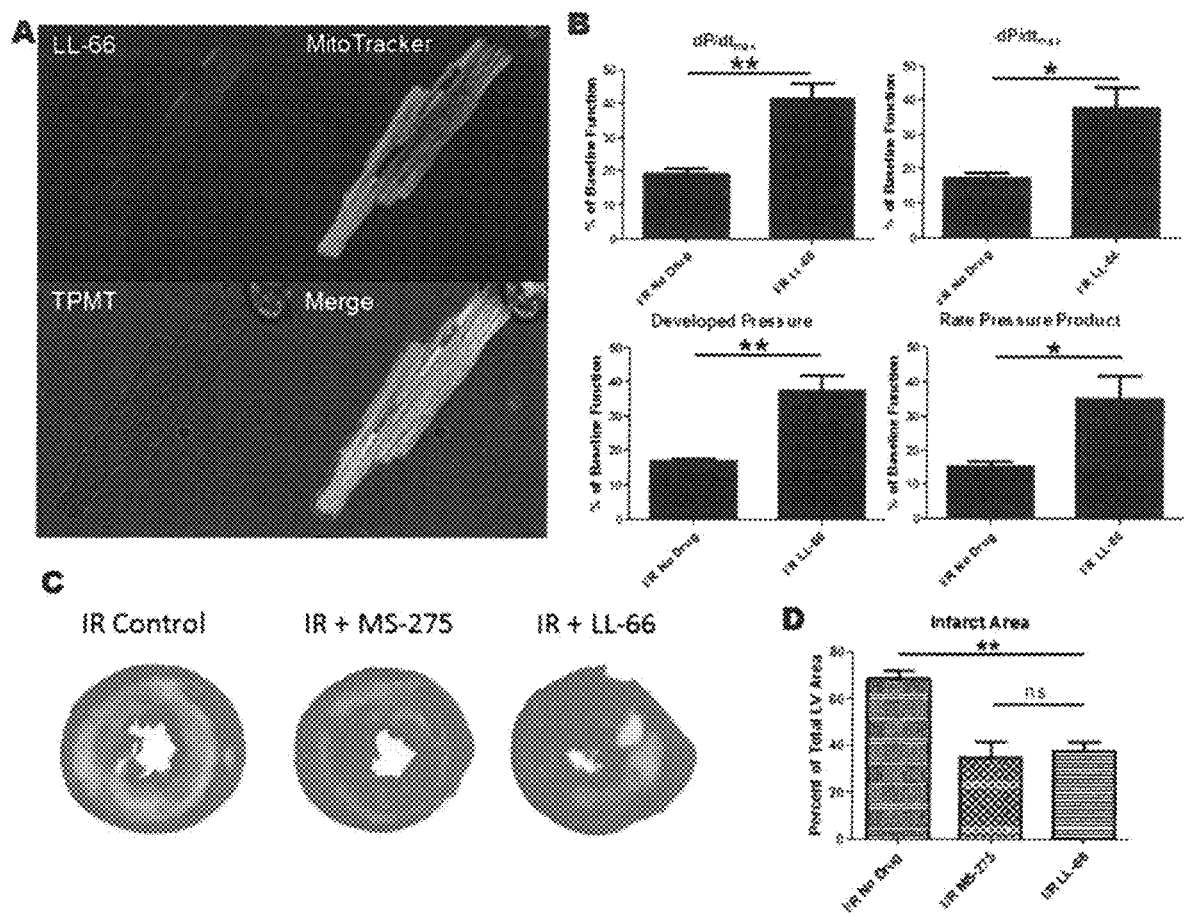
FIG. 3 provides data showing (A) Confocal fluorescent images of myocytes loaded with LL-66 and Mitotracker Deep Red FM. (B) LV functional measurements taken at the end of 30 minutes ischemia and 60 minutes of reperfusion, represented as a percentage of baseline pre-ischemia function. $dP/dt_{max}$ indicates the rate of pressure development, $dP/dt_{min}$ indicates the rate of pressure relaxation, Developed Pressure was calculated as the difference between the systolic and diastolic pressures, Rate Pressure Product was calculated as the developed pressure multiplied by the heart rate. Measurements were taken at the end of reperfusion. (C) TTC staining for infarct at the end of reperfusion; yellow/white region indicates area of infarction. Infarct areas were measured using image) software. (D) Area of Infarction for each of the groups in (C). N=3 for (A), For B-D, All data are represented as mean+/−S.D. N=4 t-test for panel B, one way ANOVA with bonferroni post-test for panel D *p<0.05.

In order to differentiate the effects of mitochondrial HDAC activity from nuclear and cytosolic HDAC activity, the inventors developed a mitochondria-targeted, class I selective HDAC inhibitor. To do this, the inventors conjugated a benzamide derivative (MS-275) to Rhodamine 123. This new inhibitor, LL-66, should localize to the mitochondria and has the added advantage of direct visualization using confocal microscopy. the inventors' data confirm that LL-66 co-localizes with Mitotracker Deep Red FM, demonstrating that LL-66 is selectively targeted to the mitochondria and is absent from the nucleus in isolated adult rat cardiac myocytes (FIG. 3A).

LL-66 allowed us to directly examine the role of mitochondrial HDAC1 activity in ischemia-reperfusion injury in the heart by again utilizing the Langendorff isolated heart model. Hearts were subjected hearts to 30 minutes of global ischemia followed by 60 minutes of reperfusion +/−LL-66. LL-66 treatment during reperfusion resulted in the same magnitude of LV functional recovery from injury as the non-targeted class I HDAC inhibitor MS-275 (FIG. 3B). Further, LL-66 treatment at reperfusion rescued viable myocardium to the same extent as MS-275 (FIG. 3C). These experiments indicate that the detrimental effects of increased HDAC activity in the first hour of reperfusion injury largely occur within the mitochondria of cardiac myocytes.

Mitochondrial Class I HDAC Inhibition Alters the Metabolic Response of Cardiac Myocytes to I/R Injury and Reduces ROS Damage.

Figure 4:
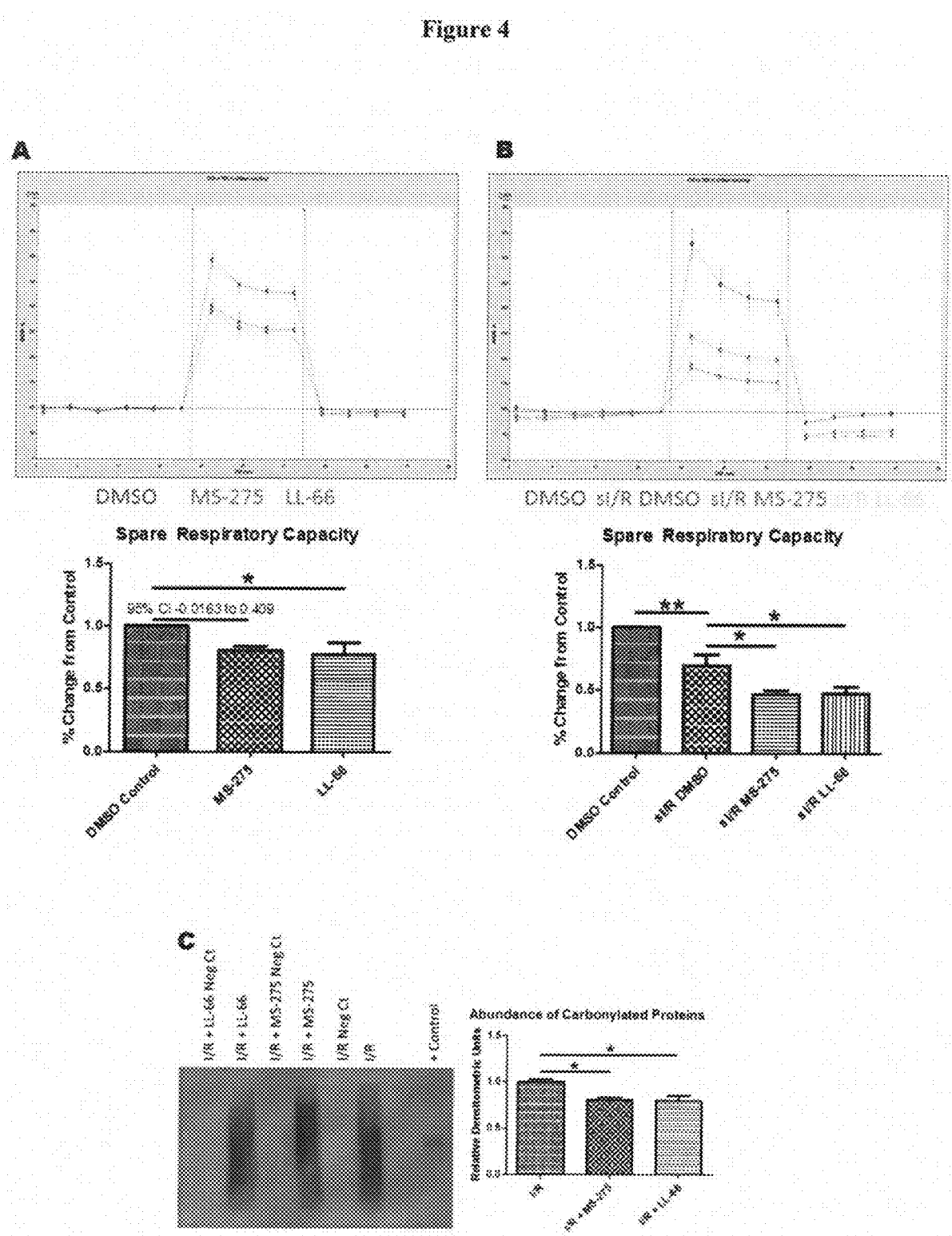
FIG. 4 shows (A) Measurements of oxygen consumption rate (OCR) in isolated cardiac myocytes. FCCP was injected at point A and antimycin D/rotenone injected at point B. (B) Measurements of OCR in isolated myocytes subjected to normoxia (blue) or chemical hypoxia. reoxygenation (red) and reperfused with DMSO (red), MS-275 (pink), or LL-66 (peach). For (A) and (B), top panels are representative, bottom panels are the uncoupled rate as a percentage of baseline rate over 4 runs. (C) Oxyblotting of tissue homogenates from Langendorff hearts subjected to I/R+/−LL-66 or MS-275. Representative seahorse data are represented mean +/−SEM, Bar graphs are represented mean +/−S.D. For all experiments, N-4, one way ANOVA with Dunnet post test *p<0.05, **p<0.01.

Since acetylation is known to regulate the activity of mitochondrial enzymes involved in multiple metabolic pathways, the inventors decided to determine if class I HDAC inhibition affects metabolic activity in cardiac myocytes both at baseline and when subjected to simulated hypoxia-reoxygenation (sI/R). For these experiments, isolated adult rat cardiac myocytes were subjected to chemical hypoxia or normoxia control for 90 minutes, then reperfused in the presence of DMSO vehicle, MS-275, or LL-66 for 60 minutes. At the conclusion of the reperfusion period, myocytes were loaded into a Seahorse extracellular flux analyzer and the oxygen consumption rate (OCR) was analyzed at baseline and in response to FCCP (injection A) and antimycin D/rotenone (injection B). The presence of either HDAC inhibitor significantly decreased the maximal uncoupled OCR, both at baseline (FIG. 4A) and following sI/R (FIG. 4B). This decrease correlates with a reduction of oxidative damage observed by oxyblotting of Lysates from Langendorff hearts subjected to I/R +/−MS-275 or LL-66 (FIG. 4C).

The inventors demonstrated that the adverse effects of increased HDAC activity begin within the first hour of reperfusion. The beneficial effects of inhibiting HDAC activity during this period may be synergistic with, or completely separate from, the established effects of inhibiting HDACs later in reperfusion[30, 31], More studies are needed to parse out the distinct pathways being affected by HDAC inhibition at these different time points of reperfusion. The inventors' study also demonstrates that a elms-selective HDAC inhibitor is beneficial in salvaging viable myocardium when administered only during the reperfusion phase. Investigating the effects of inhibiting class I HDACs in reperfusion and comparing the results to the effects of pan-HDAC inhibition may help better define the exact pathways affected by HDAC activity during reperfusion and aid in the design of better future therapies for reperfusion injury.

This is the first study to report that a class I HDAC localizes to the mitochondria in an adult mammalian organ. The rapidly expanding field of acetylation proteomics has identified acetylation as the major regulatory PTM driving metabolic programs within the mitochondria [1, 37, 38]; control of which was previously thought to be solely the purview of Sirtuin 3 [39]. Here, the inventors identified another mitochondrial deacetylase, HDAC1, which plays a critical role in regulating the metabolic response of the heart to injury. Given recent work demonstrating perturbations of the mitochondrial acetylome in heart failure [40] and other cardiac pathologies [41], the discovery of HDAC1 as a mitochondrial deactylase in cardiac myocytes opens up exciting new opportunities in both dissecting the mitochondrial elements of the pathogenesis of these diseases and designing new cardiovascular therapeutics.

Here, the inventors further demonstrated that inhibiting the activity of HDAC1, using either MS-275 or the mitochondria-targeted LL-66, results in a reduction in the spare respiratory capacity of adult rat ventricular cardiac myocytes, both at baseline and after simulated I/R. This important finding demonstrates that changing the deacetylase activity of HDAC1 in the myocyte mitochondria affects the maximal rate at which myocyte mitochondria are able to consume oxygen, indicating that HDAC1 may regulate the activity of metabolic enzymes. Further, the observed decrease in maximal respiratory rate in response to MS-275 or LL-66 treatment correlates with a reduction in oxidative damage during reperfusion ex vivo. This reduction in oxidative damage may promote myocyte survival by reducing the mitochondrial injury endured during reperfusion injury.

The data demonstrated a correlation between reduced oxygen consumption, reduced ROS stress, and preservation of myocyte viability post-I/R injury. This fits with the "gradual wakeup" hypothesis, which proposes that reduced metabolic activity during very early reperfusion reduces ROS stress and protects the heart from reperfusion injury. This is supported by evidence that cardioprotective stimuli often correlate with a reduction in activity of the electron transport chain[42]. Other evidence for reduced metabolic flux benefiting the heart in reperfusion abound, as studies have shown that inhibiting fatty acid oxidation protects the heart from injury[43], as does inhibition of the malate aspartate shuttle[44], while metabolic succinate accumulation[45] sensitizes the heart to injury. Interestingly, emerging evidence demonstrates that acetylation of proteins involved in metabolic pathways acts as a powerful regulatory signal, providing a possible direct link between mitochondrial HDAC1 and the metabolic state of the cardiac myocyte.

The data presented here demonstrated a previously unknown role for HDAC1 in directly modulating the mitochondrial acetylome, which results in an altered metabolic state in the reperfusion phase of I/R injury. This altered metabolism further correlates with reduced oxidative damage, increased viable myocardium and improved LV function post-I/R injury. The exact mechanisms by which these acetylation-induced metabolic changes affect acute I/R injury remain the subject of future work, hut this invention identifies HDAC1 as a possible therapeutic target for I/R injury and cardioprotection in the earliest hours of reperfusion.

SDHA

Figure 5:
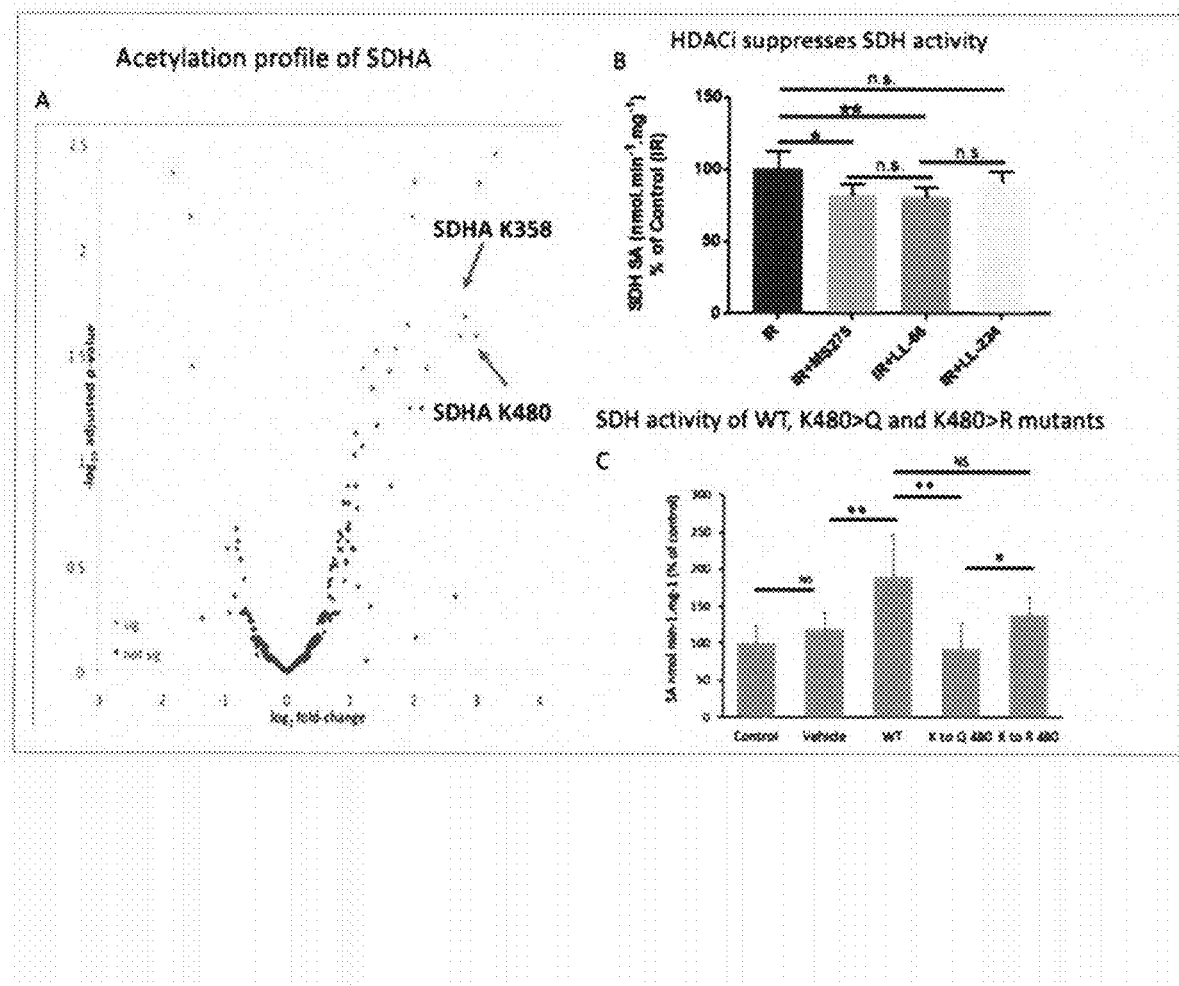
FIG. 5 shows (A) Volcano plot showing acetylated (right of center) and deacetylated (left of center) peptides in IR hearts +/−LL-66. Red dots indicate peptides with significantly changed acetylation levels. N=3 per group. (B) Treatment of Langendorff hearts with HDAC inhibitors reduce succinate dehydrogenase activity. SDH activity was measured in tissue lysates from reperfused hearts treated with either MS275 or LL-66 at reperfusion. N=4 per group. (C) SDHA activity was measured in mitochondria isolated from HEK2.93 cells expressing WT, K480Q or K480R mutants. N=4

Samples from I/R hearts treated with LL-66, LL-224, MS-275 and vehicle at reperfusion were prepared for mass spectrometry to detect changes in protein acetyl-lysine. One of the proteins that showed significant changes in acetylation in the inventors' preliminary MS data with MS-275 and LL-66 treatment was the catalytic subunit of succinate dehydrogenase flavoprotein (SDHA). Eight SDHA lysines were found to be acetylated. The inventors previously proposed to first focus on the lysine corresponding to mouse SDHA K538. It is one of the lysines that are not a Sirt3 target[5]* and it is significantly hyperacetylated in IR with LL-66 treatment compared to IR with vehicle (FIG. 5A). The inventors do not see these changes with LL-224 or vehicle. Importantly, Chouchani et. al. recently showed that the Kreb cycle intermediate succinate is consistently elevated in ischemic heart tissue and that with reperfusion the rapid oxidation of excess succinate is responsible for mitochondrial ROS production[6]*. ROS production occurs by SDH generated over-reduction of downstream electron acceptors in complex III and IV and results in driving reverse electron transport through coenzyme-Q back through complex I. The main sources of mitochondrial ROS are complex I and III[7]*, and attenuation of oxidative stress with reperfusion protects against cell death and reduces infarct size in different models of IR[8]*. Multiple studies have demonstrated that acetylation of mitochondrial enzymes is critical for regulation of oxidative phosphorylation and the Krebs cycle[9]*,[10]*. SDH is unique in that it is the only enzyme that participates both in the Krebs cycle and oxidative phosphorylation in mitochondria. Thirteen acetyl-lysine's have been identified on SDHA but there is no acetylation of SDHB[11]*, and SDHA is hyper-acetylated in the Sirt3 knockout mouse. Interestingly, hyper-acetylation inhibits SDH activity[11]*,[12]*. Horton et al recently found that overexpression of a mouse SDHA K179Q (acetylation-mirrietic) in. HEK293 lowers SDH basal activity[13]*, SDH K179 is a target of Sirt3.

Although the inventors see acetylation of the rat SDHA lysine corresponding to the mouse K179, the change in acetylation in the inventors' preliminary data between IR vs IR+MS-275 is not significant. Importantly, SDH activity is significantly reduced in Langendorff hearts treated with either MS275 or LL-66 at reperfusion (FIG. 5B). Therefore, since inhibition of the mitochondrial HDAC1 represses SDH activity and. K538 is hyperacetylated in IR when HDAC1 is inhibited, the inventors first proposed to test whether K538 acetylation represses SDH activity. The inventors have made and expressed the mouse WT, K538Q and K538R point mutants of SDHA in HEK293 cells to determine if acetylation of K538 also represses SDH activity. Contrary to what the inventors had hoped the K538Q and K538R SDHA mutants had no difference in SDHA activity from WT SDHA after normalization for expression (data not shown). The inventors then chose another SDHA lysine, K480, that was significantly hyperacetylated in IR with LL-66 (and MS-275) treatment (FIG. 5A) and not a target of Sirt3. Fortunately, the K480 point mutations displayed the activity the inventors would predict if acetylation plays a role in regulating SDHA activity. The K480R has WT activity and K.480Q has suppressed SDHA activity (FIG. 5C) when expressed in HEK293 cells.

Importantly, Chouchani et. al.[6]* have demonstrated that inhibition of SDH activity with di-methyl malonate either before ischemia in vivo or with reperfusion in isolated hearts reduces reperfusion injury results[6]*, Based on the inventors' new data demonstrating that the acetylated mimic of K480 represses SDH activity, the inventors have generated the SDHA K480R and K480Q mice. These knock-in mouse lines will allow us to directly test the hypothesis that the mechanism and major target of inhibiting mitochondrial HDAC1. activity which protects the heart in early reperfusion is preventing deacetylation of SDHA. The inventors predict that treatment of the SDHA K480R mouse (which prevents acetylation) with LL-66 would not lead to significant protection against reperfusion injury. Whereas, the SDHA K480Q (which mimics acetylation) should be protective against reperfusion injury similar to a WT mouse treated with LL-66. Further, these differential outcomes should be reflected in SDH activity during ischemia and reperfusion. If correct, this aim would identify the major pathway by which the increased activity of mitochondrial HDAC1 mediated reperfusion injury.

The invention is further described in the following numbered paragraphs:

1. A compound, or a pharmaceutically acceptable salt thereof, selected from the group consisting of:
2-(4-((2-(6-amino-3-iminio-3H-xanthen-9-yl)benzainido) methyl)benzamido) benzenaminium 2,2,2-trifluoroacetate (LL66);

2-(6-(2-(6-amino-3-iminio-3H-xanthen-9-yl)benzamido) hexanamido) benzenaminium 2,2,2-trifluoroacetate (LL38);

2-(7-(2-(6-amino-3-iminio-3H-xanthen-9-benzamido)heptanamido) benzenaminium 2,2,2-trifluoroacetate (LL45);

2-(8-(2-(6-amino-3-iminio-3H-xantheni-9-yl)benzamido) octanamido) benzenaminium 2,2,2-trifluoroacetate (LL130);

6-amino-9-(2-((4-(2-propylhydrazine-1-carbonyl)benzyl) carbamoyl)phenyl)-3H-xanthen-3-iminium 2,2,2-trifluoroacetate (LL65);

6-amino-9-(2-((7-oxo-7-(2-propylhydrazinyl)heptyl)carbamoyl)phenyl)-3H-xanthen-3-iminium 2,2,2-trifluoroacetate (LL142);

6-amino-9-(2-((2-oxo-2-((4-(2-propylhydrazine-1-carbonyl)benzypamino)ethyl) carbamoyl)phenyl)-3H-xanthen-3-iminium 2,2,2-trifluoroacetate (LL115); and 6-amino-9-(2-((2-oxo-2-((4(2-propylhydrazine-1-carbonyl) phenyl)amino)ethyl) carbamoyl)phenyl)-3H-xanthen-3-iminium 2,2,2-trifluoroacetate (LL162).

2. A pharmaceutical composition, comprising a therapeutically effective amount of a compound according to claim 1, or a pharmaceutically acceptable salt thereof, and a pharmaceutically acceptable carrier.

3. A method of inhibiting HDAC activity, comprising the step of administering a therapeutically effective amount of a compound according to claim 1, or a pharmaceutically acceptable salt thereof, to a patient in need thereof.

4. A method of treating ischemic-reperfusion injury, comprising the step of administering a therapeutically effective amount of a compound according to claim 1, or a pharmaceutically acceptable salt thereof, to a patient in need thereof.

REFERENCES

1. Choudhary, C., et al., *The growing landscape of lysine acetylation links metabolism and cell signalling.* Nat Rev Mol Cell. Biol, 2014. 15(8): p. 536-50.
2. Wellen, K. E., et al., *ATP-citrate lyase links cellular metabolism to histone acetylation.* Science, 2009. 324 (5930): p. 1076-80.
3. Zhao, S., et al. *Regulation of cellular metabolism by protein lysine acetylation.* Science, 2010. 327(5968): p. 1000-4,
4. Choudhary, C., et al., *Lysine acetylation targets protein complexes and co-regulates major cellular functions.* Science, 2009. 325(5942): p. 834-40.
5. Koprinarova, M., M, Schnekenburger, and M. Diederich, *Role of Histone Acetylation in Cell Cycle Regulation.* Curr Top Med Chem, 2015.
6. Swygert, S. G. and C. L. Peterson, *Chromatin dynamics: interplay between remodeling enzymes and histone modifications.* Biochim Biophys Acta, 2014. 1839(8): p. 728-36,
7. Corona, D. F., et al., *Modulation of ISWI function by site-specific histone acetylation.* EMBO Rep, 2002. 3(3): p. 242-7.
8. Ventura, M., et al., *Nuclear translocation of glyceraldehyde-3-phosphate dehydrogenase is regulated by acetylation.* Int J Biochem Cell Biol, 2010. 42(10): p. 1672-80.
9. Ishfaq, M., et al., *Acetylation regulates subcellular localization of eukaryotic translation initiation factor 5A (eIF5A).* FEBS Lett, 2012. 586(19): p. 3236-41.
10. Riolo, M. T., et al., *Histone deacetylase 6 (HDAC6) deacetylates survivin for its nuclear export in breast cancer.* J Biol Chem, 2012. 287(14): p. 10885-93.
11. Yi, C., et al., *Function and molecular mechanism of acetylation in autophagy regulation.* Science, 2012. 336 (6080): p. 474-7.
12. Yi, C. and L. Yu, *How does acetylation regulate autophagy?* Autophagy, 2012. 8(10): p. 1529-30.
13. Webster, B. R., et al., *Regulation of autophagy and mitophagy by nutrient availability and acetylation.* Biochim Biophys Acta, 2014. 1841(4): p. 525-34.
14. Huang, R., et al., *Deacetylation of nuclear LC3 drives autophagy initiation under starvation.* Mol Cell, 2015. 57(3): p. 456-66.
15. Allfrey, V. G., R. Faulkner, and A. B. Mirsky, *ACETYLATION AND METHYLATION OF HISTONES AND THEIR POSSIBLE ROLE IN THE REGULATION OF RNA SYNTHESIS.* Proc Natl Acad Sci USA, 1964. 51: p. 786-94.
16. Brownell, J. E., et al., *Tetrahymena histone acetyltransferase A: a homolog to yeast Gen5p linking histone acetylation to gene activation.* Cell, 1996. 84(6): p. 843-51.
17. Gu, W. and R. G. Roeder, *Activation of p53 sequence-specific DNA binding by acetylation of the p53 C-terminal domain.* Cell, 1997. 90(4): p. 595-606.
18. Spange, S., et al., *Acetylation of non-histone proteins modulates cellular signalling at multiple levels.* Int J Biochem Cell Biol, 2009. 41(1): p. 185-98.
19. Geng, H., et al., *HIF1alpha protein stability is increased by acetylation at lysine 709.* J Biol Chem, 2012. 287(42): p. 35496-505.
20. Gronroos, E., et al., *Control of Smad7 stability by competition between acetylation and ubiquitination.* Mol Cell, 2002. 10(3): p. 483-93.
21. Samant, S. A., et al., *Histone Deacetylase 3 (HDAC3)-dependent Reversible Lysine Acetylation of Cardiac Myosin Heavy Chain Isoforms Modulates Their Enzymatic and Motor Activity.* J Biol Chem, 2015. 290(25): p. 15559-69.
22. van der Heide, L. P. and M. P. Smidt, *Regulation of FoxO activity by CBP/p300-mediated acetylation.* Trends Biochem Sci, 2005. 30(2): p. 81-6.
23. Arbely, E., et al., *Acetylation of lysine 120 of p53 endows DNA-binding specificity at effective physiological salt concentration.* Proc Natl Acad Sci USA, 2011. 108(20): p. 8251-6.
24. Ray, S., et al., *Requirement of histone deacetylase1 (HDAC1) in signal transducer and activator of transcription 3 (STAT3) nucleocytoplasmic distribution.* Nucleic Acids Res, 2008. 36(13): p. 4510-20.
25. McKinsey, T. A., *Therapeutic potential for HDAC inhibitors in the heart.* Annu Rev Pharmacol Toxicol, 2012. 52: p. 303-19,
26. McKinsey, T. A., *Isoform-selective HDAC inhibitors: closing in on translational medicine for the heart.* J Mol Cell Cardiol, 2011, 51(4): p. 491-6.
27. Aurae, S. E., et al., *Selective inhibition of class I but not class IIb histone deacetylases exerts cardiac protection from ischemia reperfusion.* J Mol Cell Cardiol, 2014. 72: p. 138-45.
28. Zhao, T. C., et al., *Inhibition of histone deacetylases triggers pharmacologic preconditioning effects against myocardial ischemic injury.* Cardiovasc Res, 2007. 76(3): p, 473-81.
29. Zhang, L., et al., *Inhibition of histone deacetylases preserves myocardial performance and prevents cardiac remodeling through stimulation of endogenous angiomyogenesis.* J Pharmacol Exp Ther, 2012. 341(1): p. 285-93.

30. Granger, A., et al., *Histone deacetylase inhibition reduces myocardial ischemia-reperfusion injury in mice.* FASEB J, 2008. 22(10): p. 3549-60.
31. Xie, M., et al., *Histone deacetylase inhibition blunts ischemia/reperfusion injury by inducing cardiomyocyte autophagy,* Circulation, 2014. 129(10): p. 1139-51.
32. Still A. J., et al., *Quantification of mitochondrial acetylation dynamics highlights prominent sites of metabolic regulation.* J Biol Chem, 2013. 288(36): p, 26209-19.
33. Porter, G. A., et al., *SIRT3 deficiency exacerbates ischemic-reperlitsion injury: implication for aged hearts.* Am J Physiol Heart Circ Physiol, 2014. 306(12): p. H1602-9.
34. Bochaton, T., et al., *Inhibition of myocardial reperfusion injury by ischemic postconditioning requires sirtuin 3-mediated deacetylation of cyclophilin D.* J Mol Cell Cardiol, 2015. 84: p. 61-9.
35. Baines, C. P., et al., *Loss of cyclophilin D reveals a critical role for mitochondrial permeability transition in cell death.* Nature, 2005. 434(7033): p. 658-62.
36. Nguyen, T. T., et al., *Cyclophilin D modulates mitochondrial acetylome.* Circ Res, 2013. 113(12): p, 1308-19.
37. Anderson, K. A. and M. D. Hirschey, *Mitochondrial protein acetylation regulates metabolism.* Essays Biochem, 2012. 52: p. 23-35.
38. Menzies, K. J., et al., *Protein acetylation in metabolism—metabolites and cofactors.* Nat Rev Endocrinol, 2016. 12(1): p. 43-60.
39. Ahn, B. H., et al. *A role for the mitochondrial deacetylase Sirt3 in regulating energy homeostasis.* Proc Natl Acad Sci USA, 2008. 105(38): p. 14447-52.
40. Horton, J. L., et al., *Mitochondrial protein hyperacetylation in the failing heart.* JCI Insight, 2016. 2(1).
41. Smith, L. E. and M. Y. White, *The role of post-translational modifications in acute and chronic cardiovascular disease.* Proteomics Clin Appl, 2014. 8(7-8): p. 506-21.
42. Burwell, L. S., S. M. Nadtochiy, and P. S. Brookes, *Cardioprotection by metabolic shut-down and gradual wake-up.* J Mol Cell Cardiol, 2009. 46(6): p. 804-10.
43. Lopaschuk, G. D., et al., *Beneficial effects of trimetazidine in ex vivo working ischemic hearts are due to a stimulation of glucose oxidation secondary to inhibition of long-chain 3-ketoacyl coenzyme a thiolase.* Circ Res, 2003. 93(3): p. e33-7.
44. Nielsen, T. T., et al., *Metabolic fingerprint of ischaemic cardioprotection: importance of the malate-aspartate shuttle.* Cardiovasc Res, 2011. 91(3): p. 382-91.
45. Chouchani, E. T., et al., *Ischaemic accumulation of succinate controls reperfusion injury through mitochondrial ROS.* Nature, 2014. 515(7527): p. 431-5.

ADDITIONAL REFERENCES

1.* Burwell L S, Nadtochiy S M and Brookes P S. Cardioprotection by metabolic shut-down and gradual wake-up. *J Mol Cell Cardiol.* 2009; 46:804-10.
2.* Lopaschuk G D, Barr R, Thomas P D and Dyck J R. Beneficial effects of trimetazidine an ex vivo working ischemic hearts are due to a stimulation of glucose oxidation secondary to inhibition of long-chain 3-ketoacyl coenzyme a thiolase. *Circ Res.* 2003; 93:e33-7.
3.* Nielsen T T, Stottrup N B, Lofgren B and Botker H E. Metabolic fingerprint of ischaemic cardioprotection: importance of the malate-aspartate shuttle. *Cardiovasc Res.* 2011; 91:382-91.
4.* Boylston J A, Sun I, Chen Y, Gucek M, Sack M N and Murphy E. Characterization of the cardiac succinylome and its role in isehemia-reperfusion injury. *J Mol Cell Cardiol.* 2015; 88:73-81,
5.* Rardin M J, Newman I C, Held J M, Cusack M P, Sorensen D J, Li B, Schilling B, Mooney S D, Kahn C R, Verdin E and Gibson B W. Label-free quantitative proteomics of the lysine acetylome in mitochondria identifies substrates of SIRT3 in metabolic pathways. *Proc Natl Acad Sci USA.* 2013; 110:6601-6.
6.* Chouchani E T, Pell V R, Gaude E, Aksentijevic D, Sundier S Y, Robb E L, Logan A, Nadtochiy S M, Ord E N, Smith A C, Eyassu F, Shirley R, Hu C H, Dare A J, James A M, Rogatti S, Hartley R C, Eaton S, Costa A S, Brookes P S, Davidson S M, Duchen M R, Saeh-Parsy K, Shattock M J, Robinson A J, Work L M, Frezza. C, Krieg T and Murphy M P. Ischaemic accumulation of succinate controls reperfusion injury through mitochondrial ROS. *Nature.* 2014; 515:431-5.
7.* Chen Y R and Zweier J L. Cardiac mitochondria and reastive oxygen species generation. *Circ Res.* 2014; 114:524-37.
8.* Garciarena C D, Fantinelli J C, Caldiz C I, Chiappe de Cingolani G, Ennis I L, Perez N G, Cingolani H E and Mosca S M. Myocardial reperfusion injury: reactive oxygen species vs. NHE-1 reactivation. *Cell Physiol Biochem.* 2011; 27:13-22.
9.* Kim S C, Sprung R, Chen Y, Xu Y, Ball H, Pei. J, Cheng T, Kho Y, Xiao H, Xiao L, Grishin N V, White M, Yang X J and Zhao Y. Substrate and functional diversity of lysine acetylation revealed by a proteomics survey. *Mol cell.* 2006; 23:607-18.
10.* Choudhary C, Kumar C, Gnad F, Nielsen M L, Rehman M, Walther T C, Olsen J V and Mann M. Lysine acetylation targets protein complexes and co-regulates major cellular functions. *Science.* 2009; 325:834-40.
11.* Finley L W, Haas W, Desquiret-Dumas V, Wallace D C, Procaccio V, Gygi S P and Haigis M C. Succinate dehydrogenase is a direct target of sirtuin 3 deacetylase activity. PLUS One. 2011; 6:e23295.
12.* Cimen H, Han M J, Yang Y, Tong Q, Koc H and Koc E C. Regulation of succinate dehydrogenase activity by SIRT3 in mammalian mitochondria. *Biochemistry.* 2010; 49:304-11.
13. Horton J L, Martin O J, Lai L, Riley N M, Richards A L, Vega R B, Leone T C, Pagliarini D J, Muoio D M, Bedi K C, Jr., Margulies K B, Coon J J and Kelly D P. Mitochondrial protein hyperacetylation in the failing heart. *JCI Insight.* 2016; 2.

It is to be understood that the invention is not limited to the particular embodiments of the invention described above, as variations of the particular embodiments may be made and still fall within the scope of the appended claims.

The invention claimed is:
1. A compound, or a pharmaceutically acceptable salt thereof, selected from the group consisting of:
2-(4-((2-(6-amino-3-iminio-3H-xanthen-9-yl)benzamido) methyl)benzamido) benzenaminium 2,2,2-trifluoroacetate (LL66);
2-(6-(2-(6-amino-3-iminio-3H-xanthen-9-yl)benzamido) hexanamido) benzenaminium 2,2,2-trifluoroacetate (LL38);
2-(7-(2-(6-amino-3-iminio-3H-xanthen-9-4)benzamido) heptanamido) benzenaminium 2,2,2-trifluoroacetate (LL45);

2-(8-(2-(6-amino-3-iminio-3H-xanthen-9-yl)benzamido) octanamido) benzenaminium 2,2,2-trifluoroacetate (LL130);

6-amino-9-(2-((4-(2-propylhydrazine-1-carbonyl)benzyl) carbamoyl)phenyl)-3H-xanthen-3-iminium 2,2,2-trifluoroacetate (LL65);

6-amino-9-(2-((7-oxo-7-(2-propylhydrazinyl)heptyl)carbamoyl)phenyl)-3H-xanthen-3-iminium 2,2,2-trifluoroacetate (LL142);

6-amino-9-(2-((2-oxo-2-((4-(2-propylhydrazine-1-carbonyl)benzyl)amino)ethyl) carbamoyl)phenyl)-3H-xanthen-3-iminium 2,2,2-trifluoroacetate (LL115); and 6-amino-9-(2-((2-oxo-2-((4-(2-propylhydrazine-1-carbonyl)phenypamino)ethyl) carbamoyl)phenyl)-3H-xanthen-3-iminium 2,2,2-trifluoroacetate (LL 162).

2. A pharmaceutical composition, comprising a therapeutically effective amount of a compound according to claim 1, or a pharmaceutically acceptable salt thereof, and a pharmaceutically acceptable carrier.

3. A method of inhibiting HDAC activity, comprising the step of administering an inhibitory amount of a compound according to claim 1, or a pharmaceutically acceptable salt thereof, to a patient.

4. A method of treating ischemic-reperfusion injury, comprising the step of administering a therapeutically effective amount of a compound according to claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO. : 10,703,737 B2
APPLICATION NO. : 16/351809
DATED : July 7, 2020
INVENTOR(S) : Menick et al.

Page 1 of 1

It is certified that error appears in the above-identified patent and that said Letters Patent is hereby corrected as shown below:

In the Claims

At Column 27, Line 14, "phenypamino)ethyl)" should be printed as "phenyl)amino)ethyl)".

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*